(12) United States Patent
Hajianpour

(10) Patent No.: US 7,153,302 B1
(45) Date of Patent: *Dec. 26, 2006

(54) DEVICE FOR EXTERNAL FIXATION OF BONE FRACTURES WITH CLAMPING OF MULTIPLE PINS AND WITH A FIXTURE FOR APPLYING EXTENSION TO BONE FRAGMENTS

(75) Inventor: Mohammed Ali Hajianpour, Coral Springs, FL (US)

(73) Assignee: Phoenix Orthopaedic Corporation, Sunrise, FL (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/602,205

(22) Filed: Jun. 24, 2003

Related U.S. Application Data

(63) Continuation-in-part of application No. 09/956,314, filed on Sep. 19, 2001, now Pat. No. 6,585,736.

(51) Int. Cl.
*A61F 5/04* (2006.01)
*A61B 17/56* (2006.01)

(52) U.S. Cl. .................................. 606/57; 606/59
(58) Field of Classification Search ............ 606/53–60, 606/105
See application file for complete search history.

(56) References Cited

U.S. PATENT DOCUMENTS

| | | | |
|---|---|---|---|
| 2,406,987 A | 9/1946 | Anderson | |
| 3,877,424 A | 4/1975 | Murray | |
| 4,662,365 A | 5/1987 | Gotzen et al. | |
| 4,703,751 A * | 11/1987 | Pohl | 606/62 |
| 5,545,162 A * | 8/1996 | Huebner | 606/57 |
| 5,779,703 A * | 7/1998 | Benoist | 606/54 |
| 5,827,284 A | 10/1998 | Weigum et al. | |
| 6,190,390 B1 * | 2/2001 | McAllister | 606/87 |
| 6,197,027 B1 | 3/2001 | Hajianpour | |
| 6,423,061 B1 * | 7/2002 | Bryant | 606/57 |
| 6,440,135 B1 * | 8/2002 | Orbay et al. | 606/69 |
| 6,585,736 B1 * | 7/2003 | Hajianpour | 606/57 |

* cited by examiner

*Primary Examiner*—Pedro Philogene
(74) *Attorney, Agent, or Firm*—Ronald V. Davidge

(57) ABSTRACT

A fixture is configured to provide external fixation of a fractured end portion of a bone by including a first number of holes for pins extending from the fixture into one or more fragments in the end portion and a second number of holes for pins extending from the fixture into the bone shaft. The second number of holes includes a hole within a sliding structure allowing a single pin to be moved with a fixture to provide extension between the fragments and the shaft. A first version of the fixture includes a sliding block through which rods extend to hold pins directed laterally into the fragments(s), and a sliding for clamping pins within the first number of holes. A second version of the fixture includes an arcuate portion in which the first number of holes extend in radial directions.

17 Claims, 4 Drawing Sheets

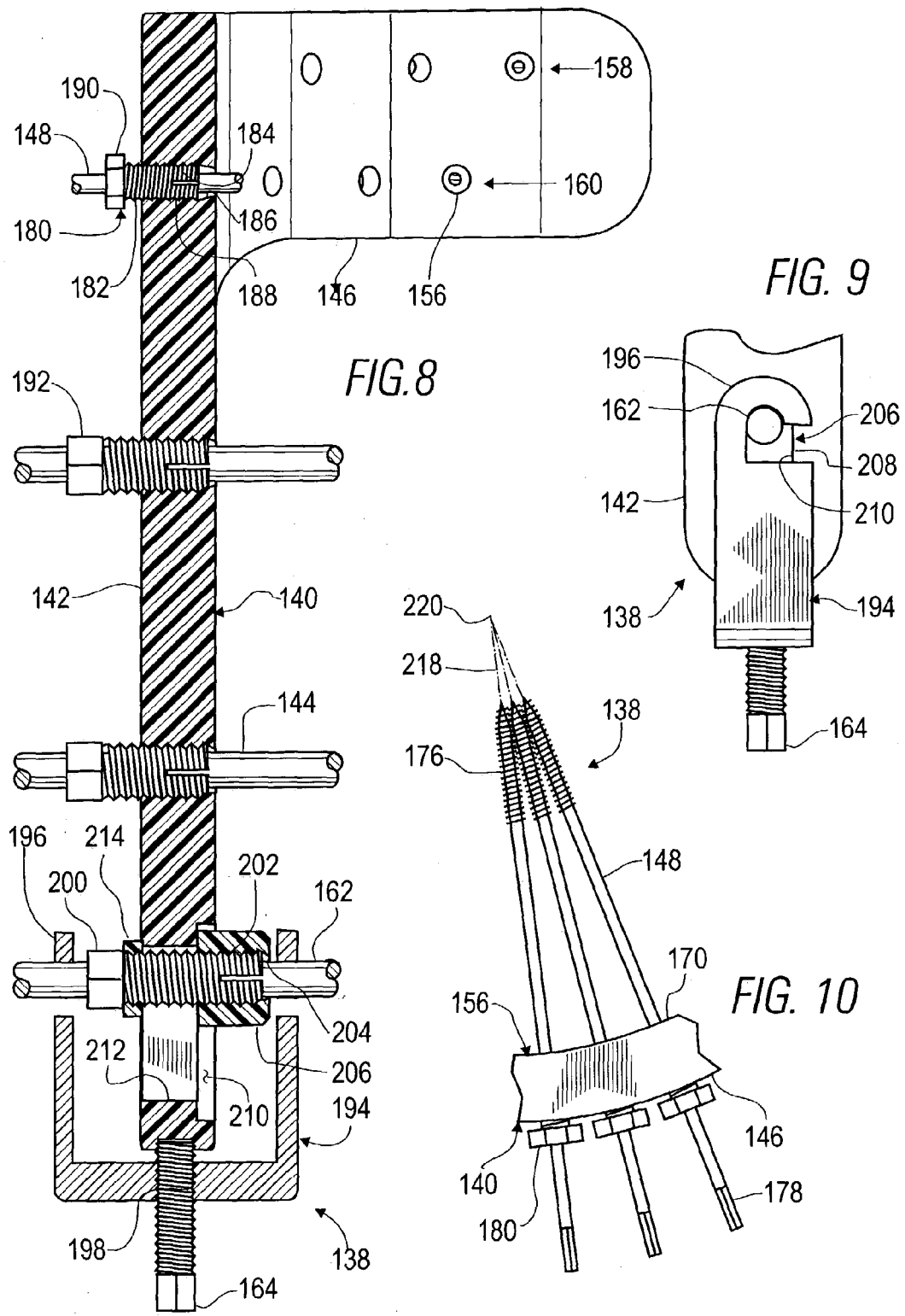

DEVICE FOR EXTERNAL FIXATION OF BONE FRACTURES WITH CLAMPING OF MULTIPLE PINS AND WITH A FIXTURE FOR APPLYING EXTENSION TO BONE FRAGMENTS

CROSS-REFERENCE TO A RELATED APPLICATION

This application is a continuation-in-part of U.S. patent application Ser. No. 09/956,314, filed Sep. 19, 2001 for which notification has been received of issue on Jul. 1, 2003 as U.S. Pat. No. 6,585,736.

BACKGROUND OF THE INVENTION

1. Field of the Invention

This invention relates to clamping pins within devices for external fixation of fractured bones, and, more particularly, to an external fixture in which pins are clamped for fixation of multiple fragments of an end portion of a bone.

2. Summary of the Background Art

The fracture of the distal radius is one of the most common human fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of Gray's Anatomy in the following manner, "The treatment consists of flexing the forearm, and making a powerful extension from the wrist and elbow, depressing at the same time the radial side of the hand, and retaining the parts in that position by well-padded pistol-shaped splints."

A common method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

The process of external pin fixation is often used in the repair of a fractured distal radius. This process initially involves the surgical insertion of skeletal traction pins on both sides of the fracture, with a frame being connected to the pins for immobilizing the bones, and for holding them together until the fracture is mended. Conventional methods for applying external pin fixation for the treatment of a fractured distal radius provide for the immobilization of the radiocarpal joint, so that the hand cannot be flexed.

While this type of fixation often provides an improvement over conventional casting techniques in the management of severe fractures of the distal radius, immobilization of the radiocarpal joint during the treatment period typically results in a long period of stiffness and disability after the external fixation device is removed. Typically, the external fixation device is left in place during the healing process for six to eight weeks. After the fixation device is removed, three to six months are required for the patient to regain motion of his hand.

An example of a fixation device providing adequate fixation during the healing process while allowing flexure in the radiocarpal joint is described in U.S. Pat. No. No. 6,197,027, the disclosure of which is incorporated herein by reference. This fixation device includes a number of pins clamped within pin mounting holes. Each pin extends through a flexible sleeve and through a clamping nut. Each pin-mounting hole includes a pilot hole guiding the pin and an internally threaded portion engaging an externally threaded portion of the clamping nut. As the clamping nut is tightened, the flexible sleeve is longitudinally compressed, so that it expands transversely to clamp itself within the pin-mounting hole and to clamp the pin within itself. The fixation device, which is configured particularly for external fixation of a fractured distal radius, includes a first number of such pins configured for attachment within a shaft portion of the radius and a second number of such pins configured to attachment to one or more fragments of the fractured radius. The fixation device also includes a sliding attachment block supporting a number of pins extending for lateral attachment to such a fragment.

However, in the holes used in the device of U.S. Pat. No. 6,197,027 to mount pins within the first number of pins, what is needed is a somewhat more simple, and therefore cost-effective, method for holding the pins in place. Such a method would preferably eliminate the need for the flexible sleeves to translate longitudinal compression into transverse clamping forces. In the holes used to mount pins within the second number of pins, what is needed is a more simple method, which will preferably clamp all of the pins in use simultaneously. Two or more of these pins may be used to clamp a single bone fragment in two or more places, or several pins may be used to clamp several bone fragments. Furthermore, since the process of setting a distal radius fracture typically includes an application of extension to the distal fragment(s), what is needed is a feature simplifying the application of such extension forces as the fixation device is installed on the fractured radius.

U.S. Pat. No. 5,545,162 describes a bone fixator including a proximal pin mounting block and a distal pin connected by a medial assembly, which connects the pin mounting blocks in a manner which is pivotally adjustable, and which further allows for adjustment of the distance between the pin mounting blocks. However, what is needed is a fixture for facilitating this distance adjustment so that it can be retained and gradually increased, instead of being lost when a clamping screw is loosened to allow movement. Furthermore, the method of U.S. Pat. No. 5,545,162 does not include the installation of pins within the fragments of bone; instead pins from the distal pin mounting block extend into the finger bones, adding a requirement that the extension forces must be directed through the wrist. To provide mobility of the hand and wrist, the fixture is pivoted with a ball joint. What is needed is a fixture rigidly holding pins extending into the bone fragments instead of into the bones of the fingers. Such a fixture would have advantages of holding different configurations of fragments in place, of holding them more rigidly, and of providing greater freedom of wrist movement.

In the lower leg, the tibia includes a long shaft and an extended upper portion which forms a plateau on which the knee pivots. Like the distal radius, this upper portion is prone to fracturing one or more fragments. Such fractures can occur when the lower leg is twisted in a manner not accommodated by the normal movement of the knee joint, as in a football injury, a slip and fall accident, or a motorcycle accident. Conventional treatment of such an injury includes surgically opening the leg adjacent the fracture and fastening various fragments of bone together with bone screws, and with a plate being fastened to the bone to serve as an abutment in holding the fragments in place. In many cases, the plate is later removed in a second surgical procedure after the bone fragments have grown together. What is needed is an apparatus and method to provide for fixation of multiple fragments from the upper tibia without a need to surgically open the area fist for installation of a plate, and then again for the removal of the plate.

U.S. Pat. No. 4,662,365 shows an external fixation device disposed external to the lower leg, including vertical support bar on which pins extending into the front of the tibia are mounted on slidably-adjustable clamping blocks and a horizontal support bar, slidably adjustable on the vertical support bar near its top. A pair of clamped pins, pivotally and slidably adjustable on the horizontal support bar, extend into the expanded upper end of the tibia at opposing angles. What is needed is a fixation device for holding a substantially larger number of pins to extend into the upper portion of the tibia from at different heights and from various angles around the leg, so that a large variety of different types of factures forming multiple bone fragments can be readily treated by fixation. Furthermore, since the process of setting an upper tibia fracture of this kind typically includes an application of extension to the fragment(s), what is needed is a feature simplifying the application of such extension forces as the fixation device is installed on the fractured tibia.

The patent art additionally describes a number of external fixation devices used for treating a fracture of the shaft portion of one of the long bones of the leg by holding pins in place above and below the fracture through an elongated structure extending externally along the leg. For example, U.S. Pat. No. 2,406,987 shows pins or wires extending through the leg and tibia above and below a fracture, with the pins or wires extending between structures of rods extending along opposite sides of the leg. The structures of rods include multiple rods held together by clamping blocks, and the pins are held in place on the rods by clamping blocks. The wires, having a relatively fine diameter, are held in place within U-shaped yokes extending around the leg between the structures of rods.

U.S. Pat. No. 4,662,365 shows an external fixation device disposed external to the lower leg, including vertical support bar on which pins extending into the front of the tibia are mounted on slidably-adjustable clamping blocks and a horizontal support bar, slidably adjustable on the vertical support bar near its top. A pair of clamped pins, pivotally and slidably adjustable on the horizontal support bar, extends into the expanded upper end of the tibia at opposing angles.

U.S. Pat. No. 5,827,284 describes a structure for adjustably clamping a bone screw in place within an external fixation device.

U.S. Pat. No. 3,877,424 describes a method and apparatus for external fixation of bone fractures. The Method comprises inserting at least one pin in each major fragment of bone with a portion of the pins extending above the skin surface, drawing the pins toward one another and applying a bridge to the pins to hold them in place under compression parallel to the bone being repaired. The apparatus is at least two elongated pins adapted to be inserted at one end into the bone on opposite sides of a fracture, bridge means engaging the other ends and compression means acting on the pins generally parallel to the bone.

SUMMARY OF THE INVENTION

According to a first aspect of the invention, a fixation device is provided for holding a first plurality of pins extending into one or more fragments of a fractured end portion of a bone and for holding a second plurality of pins extending into a shaft portion of the fractured bone. The fixation device includes a frame having an arcuate portion and an elongated portion. The arcuate portion includes an arcuate inner surface and a first plurality of holes extending radially from a center of the arcuate inner surface for holding the first plurality of pins to extend inward radially toward the center of the arcuate inner surface. The elongated portion, which extends in a first direction from the arcuate portion, includes an inner surface and a second plurality of holes for holding the second plurality of pins to extend inward from the inner surface of the elongated portion.

In the example of the fixation device installed on a fractured upper end of a tibia with the leg extending downward, the first direction is downward.

Preferably, the fixation device additionally includes a sliding pin holder slidably mounted on the elongated portion and releasably clamped in place on the elongated portion, with a hole within the second plurality of holes extending within the sliding pin holder. Sliding the sliding pin holder in the first direction increases a distance between a pin extending through the sliding pin holder and a pin extending through each hole in the first plurality of holes.

BRIEF DESCRIPTION OF THE FIGURES

FIG. 8 is a cross-sectional side elevation of the fixation device of FIG. 7;

FIG. 9 is a fragmentary rear elevation of the fixation device of FIG. 7; and FIG. 10 is a fragmentary plan view of the fixation device of FIG. 7

DETAILED DESCRIPTION OF THE INVENTION

Figure 1:
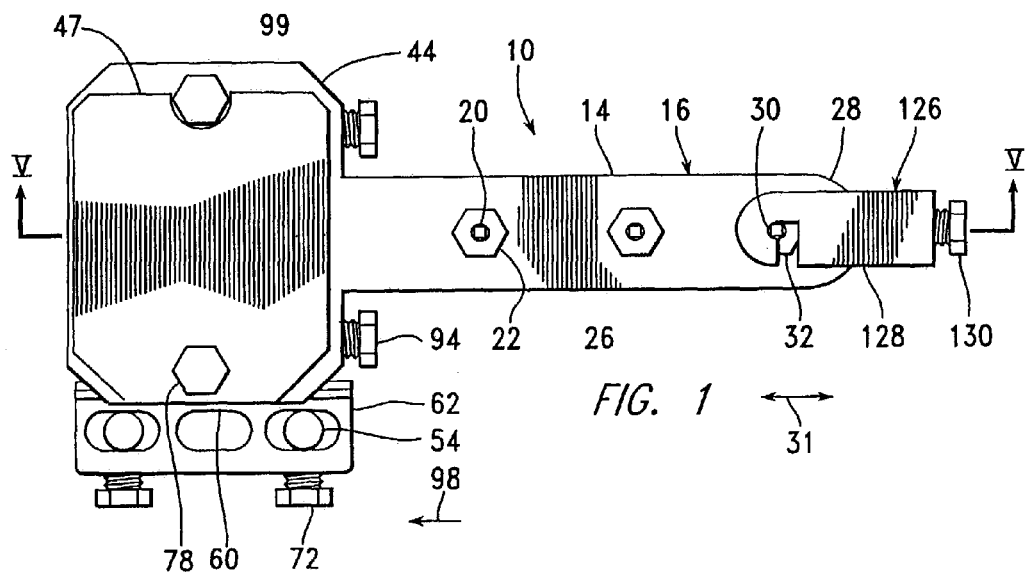
FIG. 1 is a plan view of a fixation device built in accordance with a first embodiment of the present invention.

A fixation device 10, built in accordance with a first embodiment of the present invention, will now be described, with initial reference be made to FIG. 1, a plan view of the device 10, and to FIG. 2, a front view thereof. The fixation device 10 is configured for surgical attachment to the shaft portion of a radius bone (not shown) by means of a first pattern of pins 12, extending downward from an elongated section 14 of a plate 16, with the threaded end 18 of each pin 20 being screwed into the bone by means of a conventional driving device (not shown) engaging a non-circular coupling section 22 of each pin 20. The coupling section 22 is, for example, hexagonal or square. In the central portion 26 of the elongated section 14, a pair of clamping screws 24 is used to hold the pins 20 in a fixed relationship with the plate 16. Near the proximal end 28 of the elongated section 14, a slidable pin 30 is first mounted to slide in the longitudinal directions of arrow 31, and then, after tightening, to be held in place within the plate 16 by means of a clamping screw 32 and a nut 34. The slidable pin 30 is preferably identical to the pins 22, including a threaded portion 36 fastened into the bone shaft and a non-circular coupling portion 38 for driving.

The fragment or fragments of the fractured distal radius Is/are held in place by means of a number of vertical fragment pins 40, within a second pattern of pins 42, extending downward from a widened distal portion 44 of the plate 16. Each of the pins 40 includes a threaded portion 46 for attachment within the bone fragment. In the example of FIGS. 1 and 2, the portions of pins 40 extending upward from the plate 16 are cut off after the pins 40 are fastened in place by means of non-circular coupling portions. While these coupling portions are not shown, they are understood to be similar to the coupling portions 22, 38 of the pins 20, 30, extending at the tips of the pins 40 before they are cut off. After the pins are cut off, their upward extending ends are covered with a cover plate 47.

Figure 3:
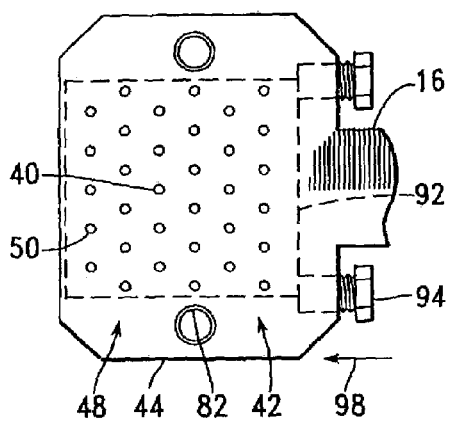
FIG. 3 is a fragmentary plan view of the fixation device of FIG. 1, showing a distal end thereof.

FIG. 3 is a fragmentary plan view of the widened distal portion 44 of the plate 16, with the cover plate 47 removed to show a pattern 48 of holes 50, extending through the plate 16 for mounting the second pattern 42 of the vertical fragment pins 40.

Figure 4:
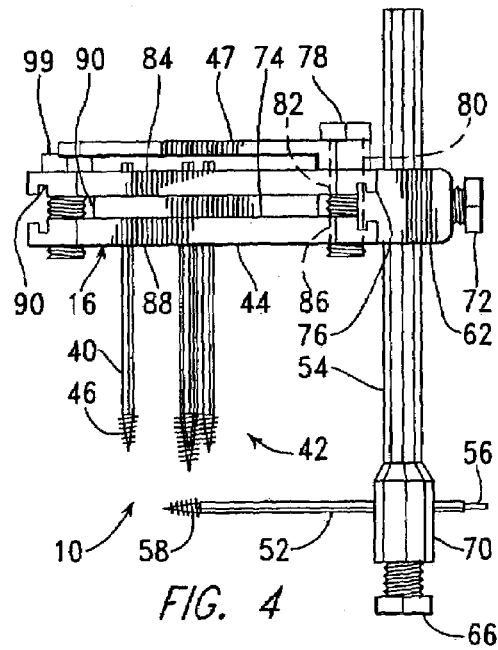
FIG. 4 is a distal end view of the distal end of the fixation device of FIG. 1.

FIG. 4 is a distal end view of the fixation device 10. One or more bone fragments can also be held in place with one, two, or three lateral fragment pins 52, extending inward from pin-mounting posts 54. These pins 52 are similar or identical to the vertical fragment pins 40, before the pins 40 are cut off, including a non-circular coupling portion 56 and threads 58 for attachment into bone.

Figure 2:
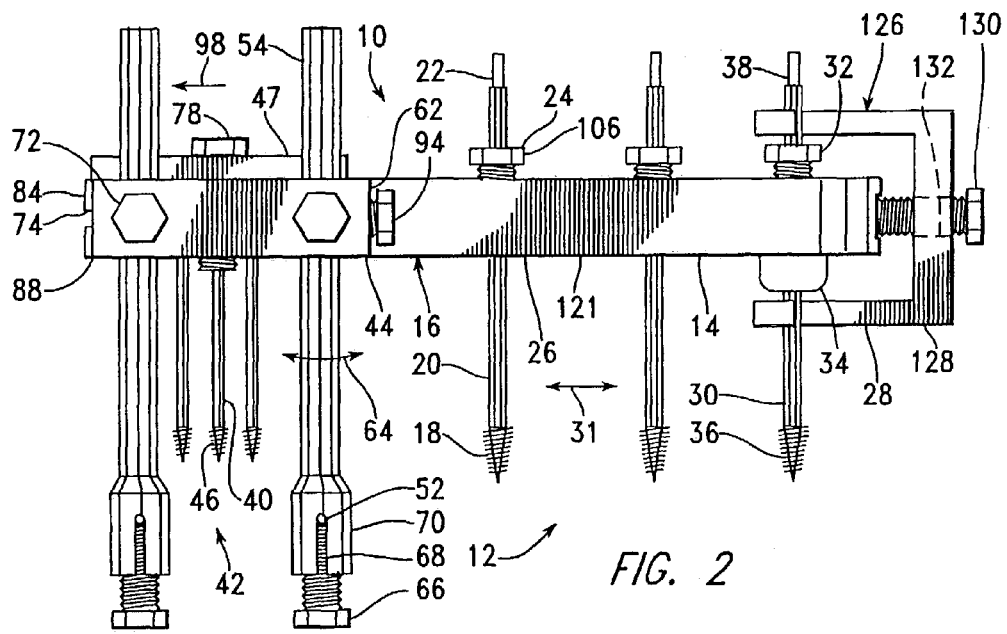
FIG. 2 is a front view of the fixation device of FIG. 1.

Referring to FIGS. 1, 2, and 4, each of the pin-mounting posts 54 is held within a slot 60 extending through a sliding block 62, which is mounted to slide in the through both the upper portion 84 and the lower portion 88 of the widened distal portion 44. After the pins 40 to be used in a particular application of the fixation device 10 are inserted through the holes 50 and 96 with these holes 50 and 96 in alignment, the plate-adjusting screws 94 are used to drive the pin-clamping plate 92 in the direction of arrow 98, simultaneously clamping all of the pins 40. After the pins 40 are clamped in place in this way, both the block clamping screw 78 and a similar screw 99 on the opposite side of the widened distal portion 44 are tightened, clamping the pin-clamping plate in place within the slot 74. After the pins 40 are clamped in this way, the screws 78 and 99 are tightened to hold both the sliding block 62 and the sliding plate 92 rigidly in place.

Each pin-clamping screw 24 includes four slots 100, extending upward from the end of a threaded portion 102 of the screw 24 in a cruciform pattern to divide the lower part of this threaded portion 102 into four segments 104. As the screw 24 is driven downward by rotating its hexagonal head 106, the four lower segments 104 come into contact with a truncated conical surface 108 within the plate 16, forcing these segments 104 inward to clamp the pin 20 extending through the screw 24.

Figure 6:
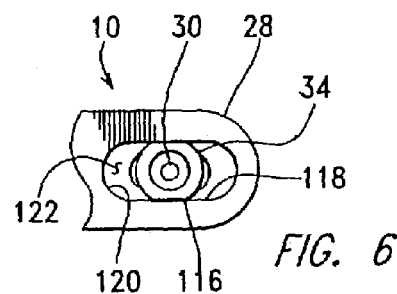
FIG. 6 is a fragmentary bottom plan view of the fixation device of FIG. 1, showing a proximal end thereof.
Figure 5:
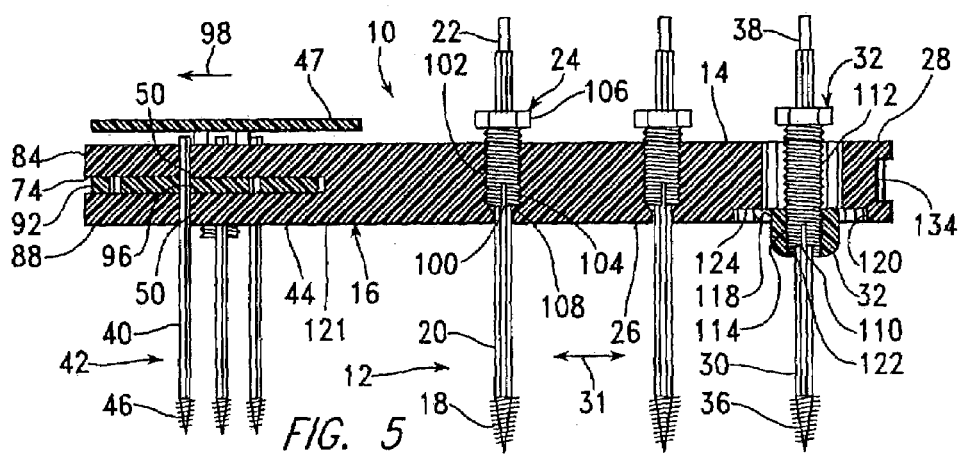
FIG. 5 is a longitudinal cross-sectional view of the fixation device of FIG. 1, taken as indicated by section lines V—V therein.

FIG. 6 is a fragmentary bottom plan view of the fixation device 10, particularly showing the proximal end 28 thereof. Referring to FIGS. 5 and 6, the pinclamping screw 32, holding the sliding pin 30, while longer than the pin-clamping screws 24, is otherwise similar to these screws 24, including four slots 110 dividing the threaded section 112 into four lower segments 114. The nut 34 includes a pair of flat sides 116, which engage flat sides 118 of an elongated slot 120, extending along a lower surface 121 of the plate 16. The lower end of the internal threads 122 of the nut 34 is tapered inward. As the clamping screw 32 is rotated into increased engagement with the nut 34, the nut 34 moves upward into engagement with a surface 124 of the elongated slot 120, and the four lower segments 114 are driven inward to hold the sliding pin 30 in place.

According to a preferred version of the present invention, the fixation device 10 includes a removable extension-setting fixture 126, shown in FIGS. 1 and 2, which is configured to set a distance between the slidable pin 30 and other features of the fixation device 10. The extension-setting fixture 126 includes a frame 128 and a setscrew 130, which extends through a threaded hole 132 within the frame 128 to engage a proximal contact surface 134 (shown in FIG. 5) of the plate 16.

A preferred method for installing the fixation device 10 to provide both support and extension to a fractured radius will now be explained, with reference being made to FIGS. 1, 2, and 4. First, the sliding pin 30 is surgically inserted and driven into the shaft portion of the radius, while the desired combination of fragment pins 40 and lateral fragment pins 52 are surgically implanted and driven into the distal fragment or fragments of the radius. The order in which these pins 30, 40, 52 are implanted and driven may be arbitrary, or may be determined by surgical considerations including the exact type of the fracture. The relationship between the sliding pin 30 and the other pins driven into the fragments must be such that the nut 32 holding the sliding pin 30 can subsequently be slid within the elongated slot 120 opposite the direction of arrow 98. Next, the setscrew 130 is tightened to move the pins 40 and 52 away from the sliding pin 30, providing a level of extension needed to properly set the fracture. Then, the pins 20 are surgically installed and driven into the radius. Finally, the setscrew 130 is loosened, and the extension-setting structure 126 is removed from the fixation device 10.

The pins 20, 30, 40, and 52 are preferably commercially available devices, which are conventionally composed of stainless steel. The frame 128 of the extension-setting fixture 126 is preferably composed of aluminum. Other portions of the fixation device 10 are preferably composed of thermoplastic resins, with the screws being composed, for example, of nylon, and with the remaining parts being composed, for example, of polycarbonate. This use of thermoplastic materials makes it possible to form X-ray images of the bones through the fixation device 10. Furthermore, such materials provide a sufficient combination of strength and resiliency to allow a pattern of pins 40 to be clamped simultaneously as described above, in spite of dimensional variations between the patterns of holes holding the pins 40 in the sliding plate 92 and in the plate 16.

The fixation device 10 of the present invention has an advantage over the prior art fixation device of U.S. Pat. No. 5,545,162 in that, in the fixation device 10, the use of the extension-setting fixture 12 allows a distance of extension to be set gradually or incrementally, without loosing the set extension distance when a clamping screw is loosened. With the fixation device 10, the distance of extension may even be set as a number of turns of the screw 130. Also, the fixation device 10 has the advantage that at pins are inserted into the bone fragments, instead of into the finger bones, allowing rigid fixation of the fragments to the remaining portion of bone while maintaining flexibility of the hand and wrist.

Figure 7:
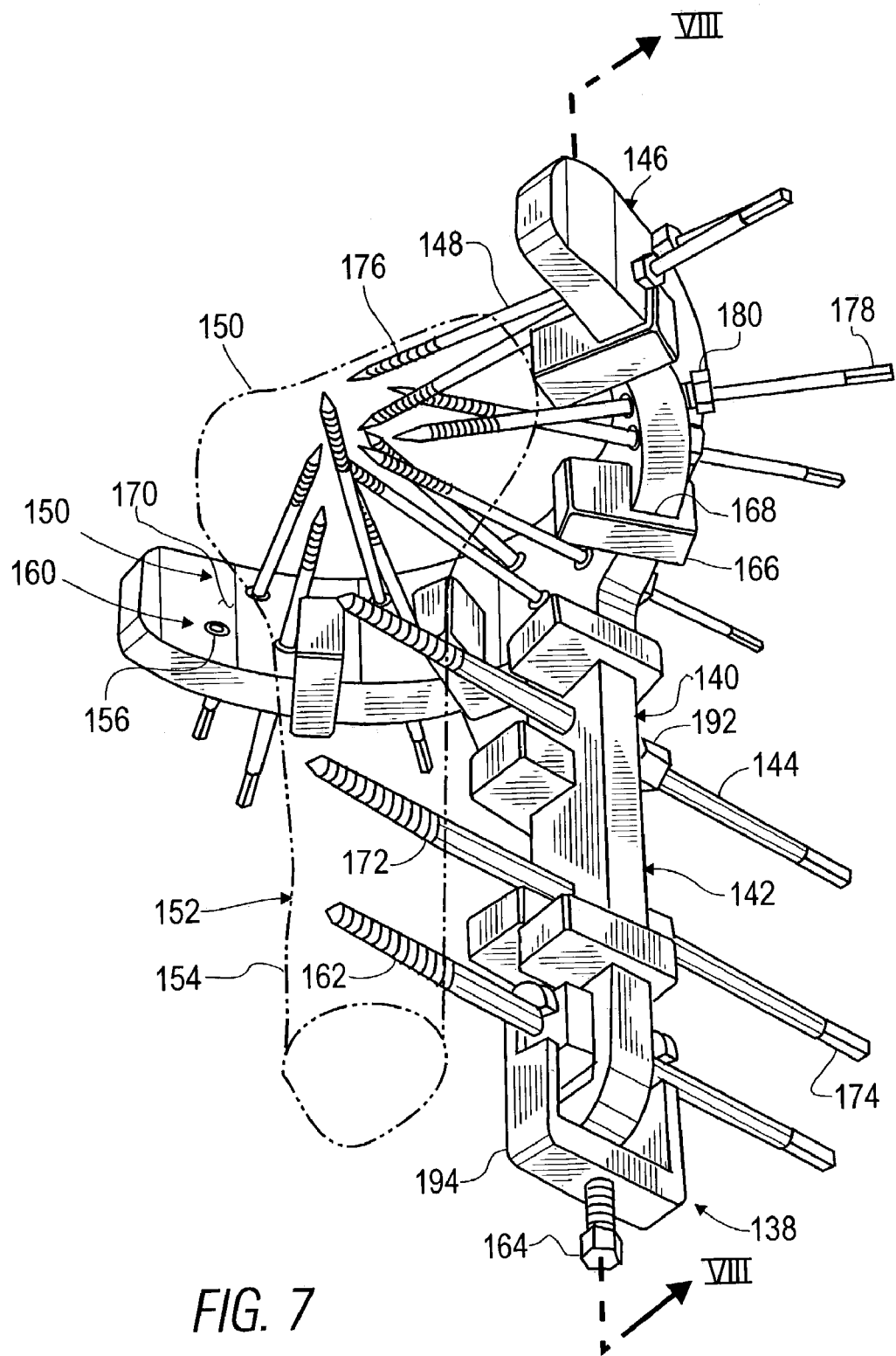
FIG. 7 is a perspective view of a fixation device built in accordance with a second embodiment of the invention.

FIG. 7 is a perspective view of a fixation device 138 built in accordance with a second version of the invention to include a frame 140 having an elongated portion 142 holding a number of lower pins 144 disposed in a linear pattern, and an arcuate portion 146 holding a number of upper pins 148 disposed in a pair of vertically-separated radial patterns. In the example of this figure, the fixation device 140 is shown as attached for fixation of a fractured upper portion 150 of a tibia 152 (shown in dashed lines) and as viewed from behind and below. (For clarity, directional conventions associated with the application of the fixation device 140 to a lower leg extending downward are used herein, without meaning to imply that the fixation device 140 needs to be installed in this orientation.) The arcuate member 146 extends outward and rearward from the top of the elongated member While the lower pins 144 are fastened into the shaft portion 154 of the tibia 152, the upper pins 148 are fastened into the upper end portion 150 thereof, with these pins 148 being particularly attached to the various fragments formed by fracturing the upper end portion 150. The actual pattern of upper pins 148 to be used is determined by the type and location of such fragments, with pin locations 156 not needed for fixation being left empty. The pin locations 156 are arranged so that the pins are radially directed in an upper pattern 158 and in a lower pattern 160, with the pins being extendable along radial lines at various angles to form interlocking structures on these two levels. Preferably, a sliding pin 162 is included among the lower pins, with the frame 140 being moved upward relative to the sliding pin 162 by tightening a setscrew 164.

Preferably, the fixation device 138 additionally includes a number of spacing blocks 166 that hold the frame 140 spaced away from the leg during the installation of the fixation device 138. Each of the spacing blocks 166 includes a slot 168 fitting around a portion of the frame 140. After the fixation device 138 is installed, the spacing blocks 166 are removed. For example, inner surface 170 of the arcuate portion 146 has a radius of 7.32 cm (2.88 in.), while each spacing block 166 spaces the frame 140 away from the leg through a distance of 1.52 cm (0.60 in.).

Each of the lower pins 144 includes a threaded portion 172 and a drive coupling portion 174, which may be non-circular for attachment of a conventional driving device for rotational attachment into the tibia 152. Similarly, each of the upper pins 148 includes a threaded portion 176 and a coupling portion 178.

FIG. 8 is a cross-sectional side elevation of the fixation device 138, taken as indicated by section lines XIII—XIII in FIG. 7. Each of the upper pins 148 is held within a pin-clamping screw 180 including a threaded portion 182 engaging a threaded hole 184 within the arcuate portion 146 of the frame 140. The threaded hole 184 includes a tapered end portion 186 that causes a flexible sections 188 at the slotted end of the threaded portion 182 of the pin-clamping screw 180 to move inward, clamping the pin 148 as the pin-clamping screw 180 is driven into engagement with the hole 184 by turning a non-circular head 190 of the pin-clamping screw 180. Except for the sliding pin 162, each of the lower pins 144 is held in place in a similar manner within a similar but larger pin-clamping screw 192.

FIG. 9 is a fragmentary rear view of the fixation device 138, particularly showing a yoke 194, used to achieve controlled movement of the frame 140, and hence of installed upper pins 148, through rotation of the setscrew 164.

Referring to FIGS. 8 and 9, the yoke 194 includes a pair of hook portions 196 extending around the sliding pin 162, and a threaded hole 198 engaging the setscrew 164, so that, as the setscrew 164 is tightened, the frame 140 is moved upward relative to the pin 162. The sliding pin 162 is held within a pin-clamping screw 200 having flexible sections 202 in a slotted end engaging the pin 162 as the screw 200 is driven into engagement with a tapered surface 204 within a sliding nut 206. The sliding nut 206 includes flat sides 208 sliding along sides 210 of a slot 212 within the frame 140 as the setscrew 164 is tightened The pin-clamping screw 200 is additionally held in sliding engagement with the frame 140 by means of a washer 214.

Except for the pins 144, 148, 162, the yoke 194 and the setscrew 164, all of which are preferably composed of metal, components of the fixation device 138 are preferably composed of radiotransparent thermoplastic resins, so that the fragments and the pins can be visualized using X-rays. To facilitate sliding, the sliding nut 206 and the washer 214 are preferably composed of a lubricious thermoplastic resin, such as acetal polymer.

The fixation device 138 is preferably surgically installed by first installing the upper pins 148 as required to hold fragments of the upper portion 150 of the fractured tibia 152 in place, with the sliding pin 162 installed within the shaft portion 154 of the tibia 152. This is done with the sliding pin 162 positioned within the slot 212 to allow for subsequent upward motion of the slot 212 on the pin 162. Next, the setscrew 164 is tightened, moving the frame and the installed upper pins 148 upward for a distance providing a controlled level of extension to the bone fragments. Next, the remaining lower screws 144 are installed in the shaft portion 154 of the tibia 152. Then, the setscrew 164 is loosened, and the yoke 194 is removed. After the bone fragments have been properly fused by the healing process, all of the pins 144, 148, and 162 are removed.

The process of installing a pin 144, 148, 162 includes driving the pin into place with a conventional screw driving tool (not shown) engaging the coupling portion of the pin. The non-circular head of the associated pin-locking screw 180, 192 is then turned with a wrench to clamp the pin 144, 148 within the fixation device 138. The non-circular head of the sliding pin-locking screw 200 is turned with a wrench to claim the sliding pin 162 within the nut 206. After the fragments are properly fused, each pin 144, 148, 162 is removed by reversing this process. Preferably, the pins 144, 148, 162 are installed with the spacing blocks 166 in place, so that the frame 140 is spaced away from the leg. Then, the blocks 166 are each removed by sliding away from the frame 140.

A significant advantage is gained over the conventional method of repairing such a fracture in that, while the method of the invention requires surgical installation and removal of screws it is no longer necessary to open the leg adjacent to the fracture to install a plate and subsequently to remove the plate.

FIG. 10 is a fragmentary plan view of the fixation device 138, showing the attachment of three upper pins 148 to extend radially inward. The distance through which the pins 148 extend inward is independently set, with the pins being clamped by rotating a clamping screw 180. Each of the upper pins 148 extends along a line 216 from a center 220 of an arc forming the arcuate inner surface 170 of the arcuate portion 146 of the frame 140.

A substantial advantage is gained over the prior art in that multiple pin locations, for pins extending at various angles in two, vertically-separated patterns are provided by the fixation device 138 instead of the two adjustable pins available on the horizontal support bar of the device described in U.S. Pat. No. 4,662,365. In the fixation device, these upper pins 148 can form an interlocking pattern holding a number of bone fragments in an established relationship. A further advantage over prior art devices is found in the use of the setscrew 164 to apply a predetermined level of extension to the fragment(s) held in place using the upper pin(s) 148.

While the fixation device 138 is described in use with a fractured upper tibia, a device of this type may be made in various sizes and used similarly, for example, with a fractured lower end of the tibia or with a fractured upper humerus.

While the present invention has been described in preferred forms or embodiments with some degree of particularity, it is understood that this description has been given only by way of example, and that numerous changes in the details of fabrication and use, including the combination and rearrangement of parts, may be made without departing from the spirit and scope of the invention.

What is claimed is:

1. A fixation device for holding a first plurality of pins extending into one or more fragments of a fractured end portion of a bone and for holding a second plurality of pins extending into a shaft portion of said fractured bone, wherein said fixation device comprises a frame including:
    an arcuate portion including an arcuate inner surface and a first plurality of holes extending radially from a center of said arcuate inner surface for holding said first plurality of pins to extend inward radially toward said center of said arcuate inner surface;
    an elongated portion, extending in a first direction from said arcuate portion, including an inner surface and a second plurality of holes for holding said second plurality of pins to extend inward from said inner surface of said elongated portion;
    a sliding pin holder slidably mounted on said main plate and releasably clamped in place on said main plate, wherein
    a hole within said second plurality of holes extends within said sliding pin holder, and
    sliding said sliding pin holder in said first direction increases a distance between a pin extending through said sliding pin holder and a pin extending through each hole in said first plurality of holes.

2. The fixation device of claim 1, wherein
    said elongated portion of said frame includes an elongated hole extending in said first direction,
    said sliding pin holder includes a nut sliding in said first direction within said elongated hole and a sliding clamping screw with threads engaging said nut, and
    said hole extending within said sliding pin holder extends through said sliding clamping screw.

3. The fixation device of claim 2, wherein an end of said sliding clamping screw is divided into a number of flexible sections moving inward to engage said pin extending through said sliding pin holder as said sliding clamping screw is driven into engagement with said nut.

4. The fixation device of claim 3, additionally comprising:
    a yoke removably attached to said pin extending through said sliding pin holder; and
    a setscrew engaging said yoke to move said frame opposite direction relative to said pin extending through said sliding pin holder.

5. The fixation device of claim 1, wherein
    said first plurality of holes extend in first pattern and second patterns displaced from one another in said first direction,
    holes within said first pattern are angularly displaced from one another along said arcuate inner surface, and
    holes within said second pattern are angularly displaced from one another along said arcuate inner surface.

6. The fixation device of claim 5, wherein holes within said second pattern are disposed at angles between adjacent holes in said first pattern.

7. The fixation device of claim 1, wherein said second plurality of holes are spaced apart in said first direction.

8. A fixation device for holding a first plurality of pins extending into one or more fragments of a fractured end portion of a bone and for holding a second plurality of pins extending into a shaft portion of said fractured bone, wherein said fixation device comprises:
    a frame including an arcuate portion including an arcuate inner surface and a first plurality of holes extending radially from a center of said arcuate inner surface for holding said first plurality of pins to extend inward radially toward said center of said arcuate inner surface, wherein each hole within said first plurality of holes includes an internally threaded portion, and an elongated portion, extending in a first direction from said arcuate portion, including an inner surface and a second plurality of holes for holding said second plurality of pins to extend inward from said inner surface of said elongated portion; and
    a pin-clamping screw within said internally threaded portion of a hole within said first plurality of holes, wherein said pin-clamping screw includes a hole for holding a pin within said first plurality of pins, and wherein an end of said pin-clamping screw is divided into a number of flexible sections moving inward to engage a pin extending through said hole within said pin-clamping screw as said pin-clamping screw is driven into engagement with said internally traded portion of said hole within said first plurality of holes.

9. A fixation device for holding a first plurality of pins extending into one or more fragments of a fractured end portion of a bone and for holding a second plurality of pins extending into a shaft portion of said fractured bone, wherein said fixation device comprises:
    a frame including an arcuate portion including an arcuate inner surface and a first plurality of holes extending radially from a center of said arcuate inner surface for holding said first plurality of pins to extend inward radially toward said center of said arcuate inner surface, and an elongated portion, extending in a first direction from said arcuate portion, including an inner surface and a second plurality of holes for holding said second plurality of pins to extend inward from said inner surface of said elongated portion, wherein each hole within said second plurality of holes includes an internally threaded portion; and
    a pin-clamping screw within said internally threaded portion of a hole within said second plurality of holes, wherein said pin-clamping screw includes a hole for holding a pin within said second plurality of pins, and wherein an end of said pin-clamping screw is divided into a number of flexible sections moving inward to engage a pin extending through said hole within said pin-clamping screw as said pin-clamping screw is driven into engagement with said internally traded portion of said hole within said second plurality of holes.

10. A fixation device for holding a first plurality of pins extending into one or more fragments of a fractured end portion of a bone and for holding a second plurality of pins extending into a shaft portion of said fractured bone, wherein said fixation device comprises:
    a frame including an arcuate portion including an arcuate inner surface and a first plurality of holes extending radially from a center of said arcuate inner surface for holding said first plurality of pins to extend inward radially toward said center of said arcuate inner surface, and an elongated portion, extending in a first direction from said arcuate portion, including an inner surface and a second plurality of holes for holding said second plurality of pins to extend inward from said inner surface of said elongated portion; and a plurality of removably attached spacing blocks for holding said frame spaced away from a body part to which said fixation device is attached.

11. A method for fixing one or more fragments of a fractured end portion of a bone in place with respect to a shaft portion of said bone, wherein said method comprises:
 a) surgically inserting a first plurality of pins through holes within a first plurality of holes extending within an arcuate portion of a fixture into said fractured end portion of said bone, wherein said arcuate portion includes an arcuate inner surface, and wherein said first plurality of holes extend radially from a center of said arcuate inner surface;
 b) clamping each pin within said first plurality of pins in place within a hole within said first plurality of holes;
 c) surgically inserting a sliding pin to extend through a hole within a sliding pin holder, mounted to slide along said main plate of said fixation device, into said shaft portion of said bone;
 d) after completing step c), sliding said sliding pin holder to establish extension between bone fragments of in said fractured end portion of said bone and shaft of said bone;
 e) clamping said sliding pin holder in a location established in step d) to maintain said extension;
 f) surgically inserting a second pin to extend through a hole within a second plurality of holes in an elongated portion of said fixture to extend into a shaft portion of said bone; and
 g) clamping said second pin to extend through said hole within said second plurality of holes.

12. The method of claim 11, wherein step d) includes attaching a yoke to said sliding pin; and
 driving a setscrew to slide said yoke with said sliding pin and said sliding pin holder relative to said elongated portion of said fixture.

13. The method of claim 12, additionally comprising removing said yoke from said sliding pin.

14. The method of claim 11, wherein step g) includes:
 rotating a sliding pin clamping screw, engaging a nut mounted to slide within an elongated slot in said first plate, in an engagement direction,
 rotating said sliding pin clamping screw in said engagement direction pulls said nut to move into engagement with a surface of said elongated slot, clamping said nut in place within said elongated slot, and
 rotating said sliding pin clamping screw in said engagement direction drives flexible sections of said sliding pin clamping screw inward to clamp said sliding pin within a hole extending through said sliding pin clamping screw.

15. A method for fixing one or more fragments of a fractured end portion of a bone in place with respect to a shaft portion of said bone, wherein said method comprises:
 a) surgically inserting a first plurality of pins through holes within a first plurality of holes extending within an arcuate portion of a fixture into said fractured end portion of said bone, wherein said arcuate portion includes an arcuate inner surface, and wherein said first plurality of holes extend radially from a center of said arcuate inner surface;
 b) clamping each pin within said first plurality of pins in place within a hole within said first plurality of holes by rotating a pin clamping screw in engagement with a threaded portion of said hole within said first plurality of holes to drive flexible sections of said pin clamping screw inward to clamp each of said first plurality of pins within a hole extending through said pin clamping screw;
 c) surgically inserting a second pin to extend through a hole within a second plurality of holes in an elongated portion of said fixture to extend into a shaft portion of said bone; and
 d) clamping said second pin to extend through said hole within said second plurality of holes.

16. A method for fixing one or more fragments of a fractured end portion of a bone in place with respect to a shaft portion of said bone, wherein said method comprises:
 a) surgically inserting a first plurality of pins through holes within a first plurality of holes extending within an arcuate portion of a fixture into said fractured end portion of said bone, wherein said arcuate portion includes an arcuate inner surface, and wherein said first plurality of holes extend radially from a center of said arcuate inner surface;
 b) clamping each pin within said first plurality of pins in place within a hole within said first plurality of holes;
 c) surgically inserting a second pin to extend through a hole within a second plurality of holes in an elongated portion of said fixture to extend into a shaft portion of said bone; and
 d) clamping said second pin to extend through said hole within said second plurality of holes by rotating a pin clamping screw in engagement with a threaded portion of said hole within said second plurality of holes to drive flexible sections of said pin clamping screw inward to clamp said second pin within a hole extending through said sliding pin clamping screw.

17. A method for fixing one or more fragments of a fractured end portion of a bone in place with respect to a shaft portion of said bone, wherein said method comprises:
 a) surgically inserting a first plurality of pins through holes within a first plurality of holes extending within an arcuate portion of a fixture into said fractured end portion of said bone, wherein said arcuate portion includes an arcuate inner surface, and wherein said first plurality of holes extend radially from a center of said arcuate inner surface;
 b) clamping each pin within said first plurality of pins in place within a hole within said first plurality of holes;
 c) surgically inserting a second pin to extend through a hole within a second plurality of holes in an elongated portion of said fixture to extend into a shaft portion of said bone;
 d) clamping said second pin to extend through said hole within said second plurality of holes; and
 e) removing a plurality of removably attached spacing blocks for holding said frame spaced away from a body part to which said fixation device is attached.

* * * * *